US006666831B1

(12) United States Patent
Edgerton et al.

(10) Patent No.: US 6,666,831 B1
(45) Date of Patent: Dec. 23, 2003

(54) METHOD, APPARATUS AND SYSTEM FOR AUTOMATION OF BODY WEIGHT SUPPORT TRAINING (BWST) OF BIPED LOCOMOTION OVER A TREADMILL USING A PROGRAMMABLE STEPPER DEVICE (PSD) OPERATING LIKE AN EXOSKELETON DRIVE SYSTEM FROM A FIXED BASE

(75) Inventors: V. Reggie Edgerton, Los Angeles, CA (US); M. Kathleen Day, Santa Monica, CA (US); Susan Harkema, Los Angeles, CA (US); Antal K. Bejczy, Pasadena, CA (US); James R. Weiss, Pasadena, CA (US)

(73) Assignees: The Regents of the University of California, Oakland, CA (US); California Institute of Technology, Pasadena, CA (US)

( * ) Notice: Subject to any disclaimer, the term of this patent is extended or adjusted under 35 U.S.C. 154(b) by 251 days.

(21) Appl. No.: 09/643,134

(22) Filed: Aug. 21, 2000

Related U.S. Application Data

(60) Provisional application No. 60/150,085, filed on Aug. 20, 1999.

(51) Int. Cl.[7] .................................................. A61B 5/00

(52) U.S. Cl. ..................... 600/587; 600/595; 73/379.01

(58) Field of Search ......................... 482/1–9, 900–902; 600/587, 595; 73/379.01–379.03

(56) References Cited

U.S. PATENT DOCUMENTS 5,792,031 A 8/1998 Alton

OTHER PUBLICATIONS

Harkema, Susan J. et al.; "Locomotor Training Manual," distributed to Clinical Trial, Physical Rehabilitation Specialists, 1999.

Jau, Bruno M. et al.; "Exoskeletal System for Neuromuscular Rehabilitation," Jet Propulsion Laboratory Technology Report; May 1999; pp. 1–11.

Bejcay, Antal K.; "Towards Development of Robotic Aid for Rehabihilitation," Jet Propulsion Laboratory, California Institute of Technology, Jun. 28–29, 1999.

*Primary Examiner*—Glenn E. Richman
(74) *Attorney, Agent, or Firm*—Fulbright & Jaworski

(57) ABSTRACT

A robotic exoskeleton and a control system for driving the robotic exoskeleton, including a method for making and using the robotic exoskeleton and its control system. The robotic exoskeleton has sensors embedded in it which provide feedback to the control system. Feedback is used from the motion of the legs themselves, as they deviate from a normal gait, to provide corrective pressure and guidance. The position versus time is sensed and compared to a normal gait profile. Various normal profiles are obtained based on studies of the population for age, weight, height and other variables.

27 Claims, 8 Drawing Sheets

METHOD, APPARATUS AND SYSTEM FOR AUTOMATION OF BODY WEIGHT SUPPORT TRAINING (BWST) OF BIPED LOCOMOTION OVER A TREADMILL USING A PROGRAMMABLE STEPPER DEVICE (PSD) OPERATING LIKE AN EXOSKELETON DRIVE SYSTEM FROM A FIXED BASE

This application claims the benefit of Ser. No. 60/150,085 (filed Aug. 20, 1999).

This invention was made with Government support under Grant. No. NS16333, awarded by the National Institutes of Health. The Government has certain rights in this invention.

FIELD OF INVENTION

The field of the invention is robotic devices to improve ambulation.

BACKGROUND

There is a need to train patients who have had spinal cord injuries or strokes to walk again. The underlying scientific basis for this approach is the observation that after a complete thoracic spinal cord transection, the hindlimbs of cats can be trained to fully support their weight, rhythmically step in response to a moving treadmill and adjust their walking speed to that of a treadmill. See for example, Edgerton et al., Recovery of full weight-supporting locomotion of the hindlimbs after complete thoracic spinalization of adult and neonatal cats. In: *Restorative Neurology, Plasticity of Motoneuronal Connections*. New York, Elsevier Publishers, 1991, pp. 405–418; Edgerton, et al., Does motor learning occur in the spinal cord? *Neuroscientist* 3:287–294, 1997b; Hodgson, et al., Can the mammalian lumbar spinal cord learn a motor task? *Med. Sci. Sports Exerc*. 26:1491–1497, 1994.

Relatively recently, a new rehabilitative strategy, locomotor training of locomotion impaired subjects using Body Weight Support Training (BWST) technique over a treadmill has been introduced and investigated as a novel intervention to improve ambulation following neurologic injuries. Results from several laboratories throughout the world suggest that locomotor training with a BWST technique over a treadmill significantly can improve locomotor capabilities of both acute and chronic incomplete spinal cord injured (SCI) patients.

Current BWST techniques rely on manual assistance of several therapists during therapy sessions. Therapists provide manual assistance to the legs to generate the swing phase of stepping and to stabilize the knee during stance. This manual assistance has several important scientific and functional limitations. First, the manual assistance provided can vary greatly between therapists and sessions. The patients' ability to step on a treadmill is highly dependent upon the skill level of the persons conducting the training. Second, the therapists can only provide a crude estimate of the required force torque and acceleration necessary for a prescribed and desired stepping performance. To date all studies and evaluations of step training using BWST technique over a treadmill have been limited by the inability to quantify the joint torques and kinematics of the lower limbs during training. This information is critical to fully assess the changes and progress attributable to step training with BWST technique over a treadmill. Third, the manual method can require up to three or four physical therapists to assist the patient during each training. session. This labor-intensive protocol is too costly and impractical for widespread clinical applications.

There is a need for a mechanized system with sensor-based automatic feedback control exists to assist the rehabilitation of neurally damaged people to relearn the walking capability using the BWST technique over a treadmill. Such a system could alleviate the deficiencies implied in the currently employed manual assistance of therapists. A programmable stepper device would utilize robotic arms instead of three physical therapists. It would provide rapid quantitative measurements of the dynamics and kinematics of stepping. It would also better replicate the normal motion of walking for the patients, with consistency.

SUMMARY OF THE INVENTION

The invention is a robotic exoskeleton and a control system for driving the robotic exoskeleton. It includes the method for making and using the robotic exoskeleton and its control system. The robotic exoskeleton has sensors embedded in it which provide feedback to the control system.

The invention utilizes feedback from the motion of the legs themselves, as they deviate from a normal gait, to provide corrective pressure and guidance. The position versus time is sensed and compared to a normal gait profile. There are various normal profiles based on studies of the population for age, weight, height and other variables. While the portion of the legs is driven according to a realistic model human gait, additional mechanical assistance is applied to flexor and extensor muscles and tendons at an appropriate time in the gait motion of the legs in order to stimulate the recovery of afferent-efferent nerve pathways located in the lower limbs and in the spinal cord. The driving forces applied to move the legs are positioned to induce activations of these nerve pathways in the lower limbs that activate the major flexor and extensor muscle groups and tendons, rather than lifting from the bottom of the feet.

BRIEF DESCRIPTION OF THE DRAWINGS

The above and other features and advantages. of the invention will be more apparent from the following detailed description wherein.

DETAILED DESCRIPTION OF A PREFERRED EMBODIMENT

The following description is of the best mode presently contemplated for carrying out the invention. This description is not to be taken in a limiting sense, but is merely made for the purpose of describing the general principles of the invention. The scope of the invention should be determined with reference to the claims.

The solution to the above problem is an individually adjustable and automated BWST technique using a Programmable Stepping Device (PSD) with model and sensing based control operating like an exoskeleton on the patients' legs from a fixed base on the treadmill (i) to replace the active and continuous participation of currently needing several highly and specifically trained therapists to conduct the retraining sessions, (ii) to provide a consistent training performance, and (iii) to establish a quantified data base for evaluating patient's progress during locomotor. training.

The system serves the purpose of assisting and easing the rehabilitation of spinal cord, stroke and traumatic brain injured people (as well as others with injury affecting locomotion) to regain, walking capabilities. The overall system uses an individually adjustable and sensing based automation of body weight support training (BWST) to train standing and locomotion of impaired patients. The system helps them to relearn how to walk on a treadmill which then facilitates relearning to walk overground. It uses an individually adjustable and sensing based automation of body weight support training (BWST) approach to train standing and locomotion of impaired patients by helping them to relearn how to walk on a treadmill which then facilitates relearning to walk overground.

Figure 1:
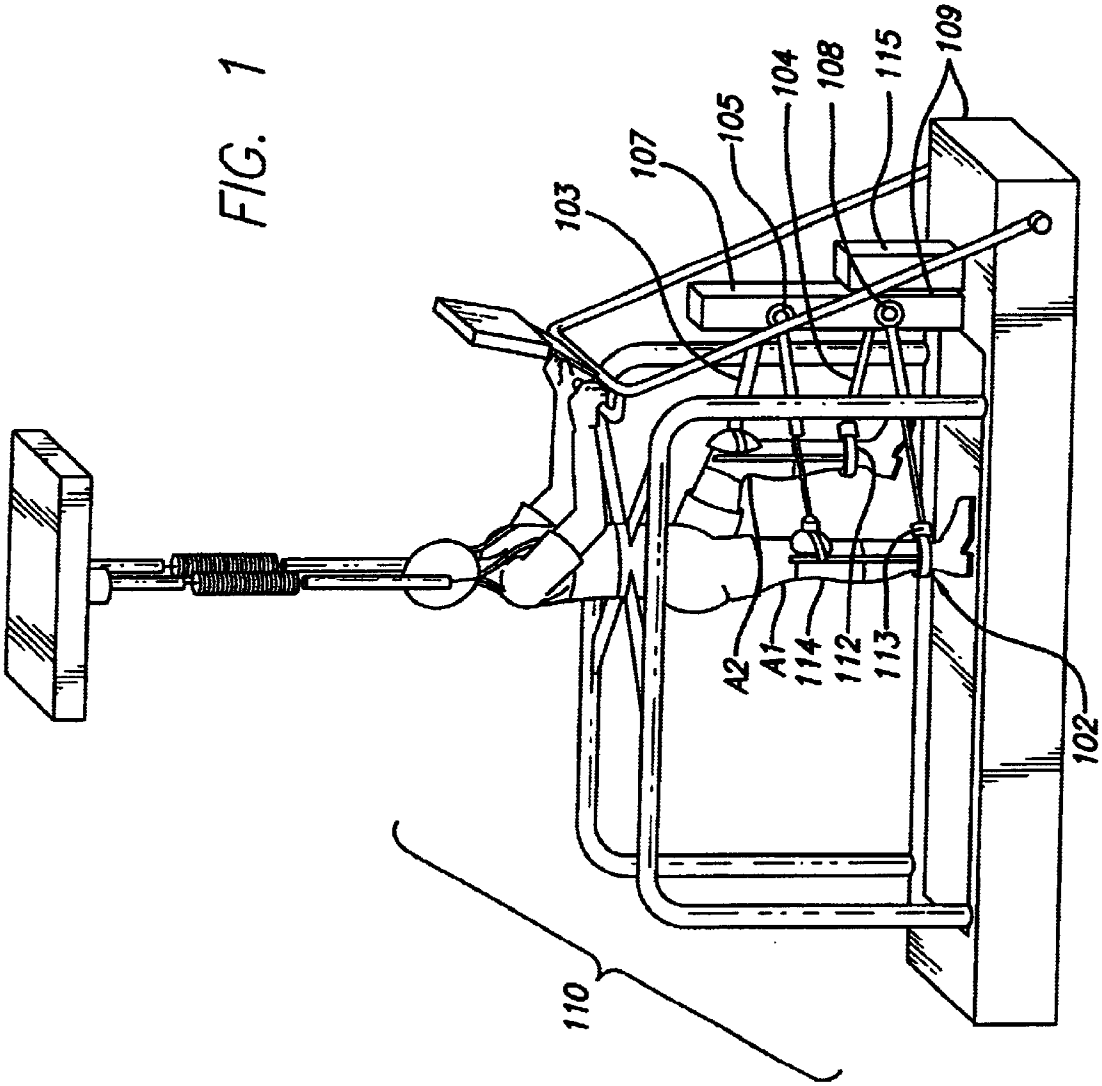
FIG. 1 shows the patient in a body weight suspension training (BWST) modality over a treadmill attached to two pairs of robotic arms, with sensors, which are computer controlled and are directed to train the patient to walk again.
Figure 2:
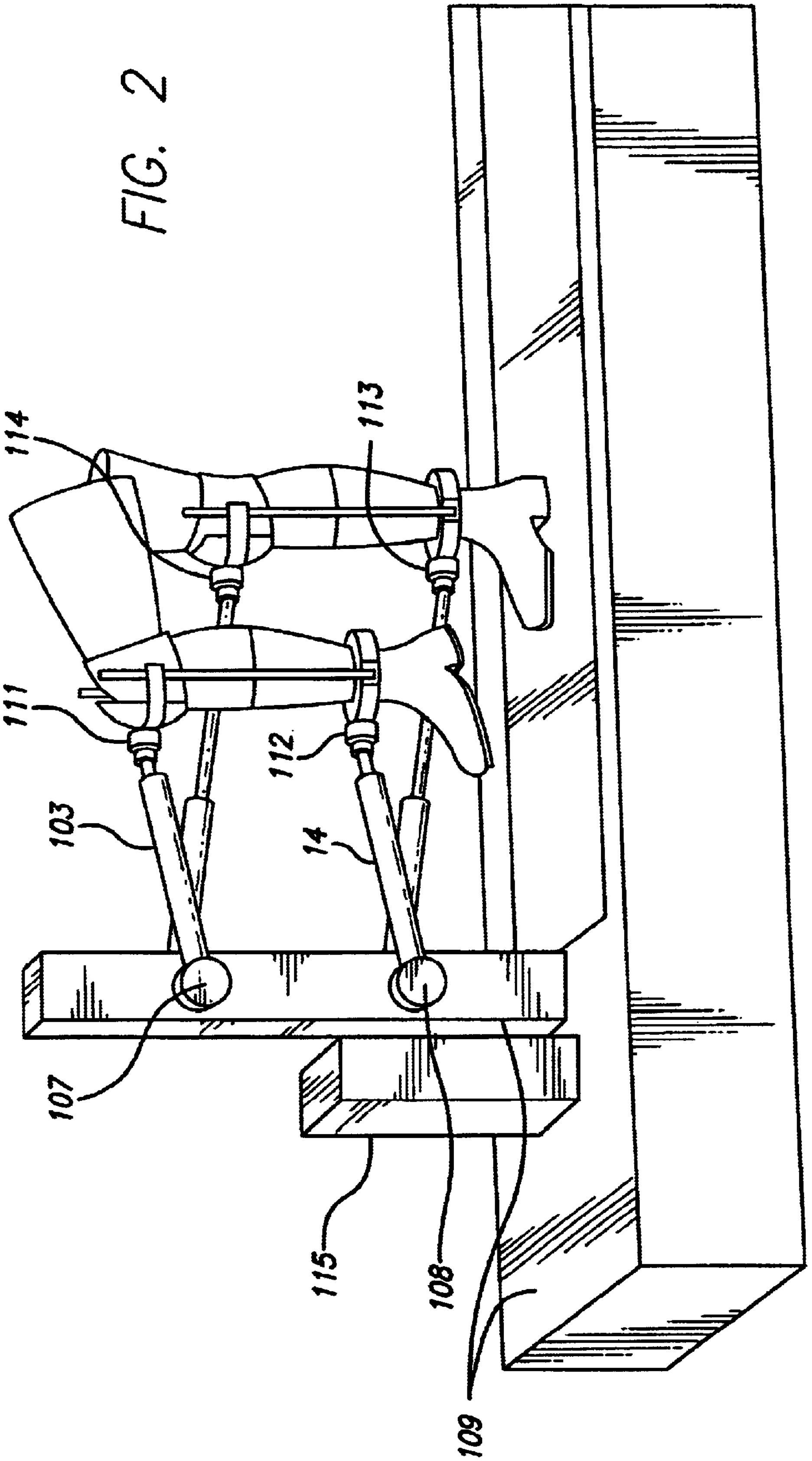
FIG. 2 shows another view of the legs of the patient attached to the robotic arms which have the acceleration and force/torque sensors in them.

FIG. 1 and FIG. 2 show two pairs of motor-driven mechanical linkage units, each unit with two mechanical degrees-of-freedom, are connected with their drive elements to the fixed base of the treadmill while the linkages' free ends are attached to the patient's lower extremities. Two pairs of motor-driven mechanical linkage units 101, 102, 103, 104 each unit with two mechanical degrees-of-freedom, are connected with their drive elements 105, 106, 107, 108 to the fixed base 109 of the treadmill 110 while the linkages' free ends 111, 112, 113, 114 are attached to the patient's lower extremities (legs) A1, A2 at two locations at each leg so that one linkage pair 101, 102 serves one leg A1 and the other linkage pair 103,104 serves the other leg A2 in the sagittal plane of bipedal locomotion.

Thus, this linkage system arrangement 101, 102, 103, 104 is capable of reproducing the profile of bipedal locomotion and standing in the sagittal plane from a fixed base 109 which is external to the act of bipedal locomotion and standing on a treadmill 110.

The exoskeleton linkage system together with its passive compliant elements are adjustable to the geometry and dynamic needs of individual patients.

This individual adjustment is implemented in this embodiment with the control of the linkage system of the programmable stepper device (PSD) computer 115 based, referenced to individual stepping models, treadmill 110 speed, and force/torque and acceleration data (sensors located at 111, 112, 113, 114) sensed at the linkages' exoskeleton contact area with each of the patient's legs 111, 112, 113, 114.

As seen in FIG. 2 the system concept is built on the use of special two degree-of-freedom (d.o.f) robot arms 101, 103, 102, 104 connected to the fixed base of the treadmill where their drive system is located, while the free end of the robot arms 111, 112, 113, 114 is connected to the patient's legs like an exoskeleton attachment.

Figure 3:
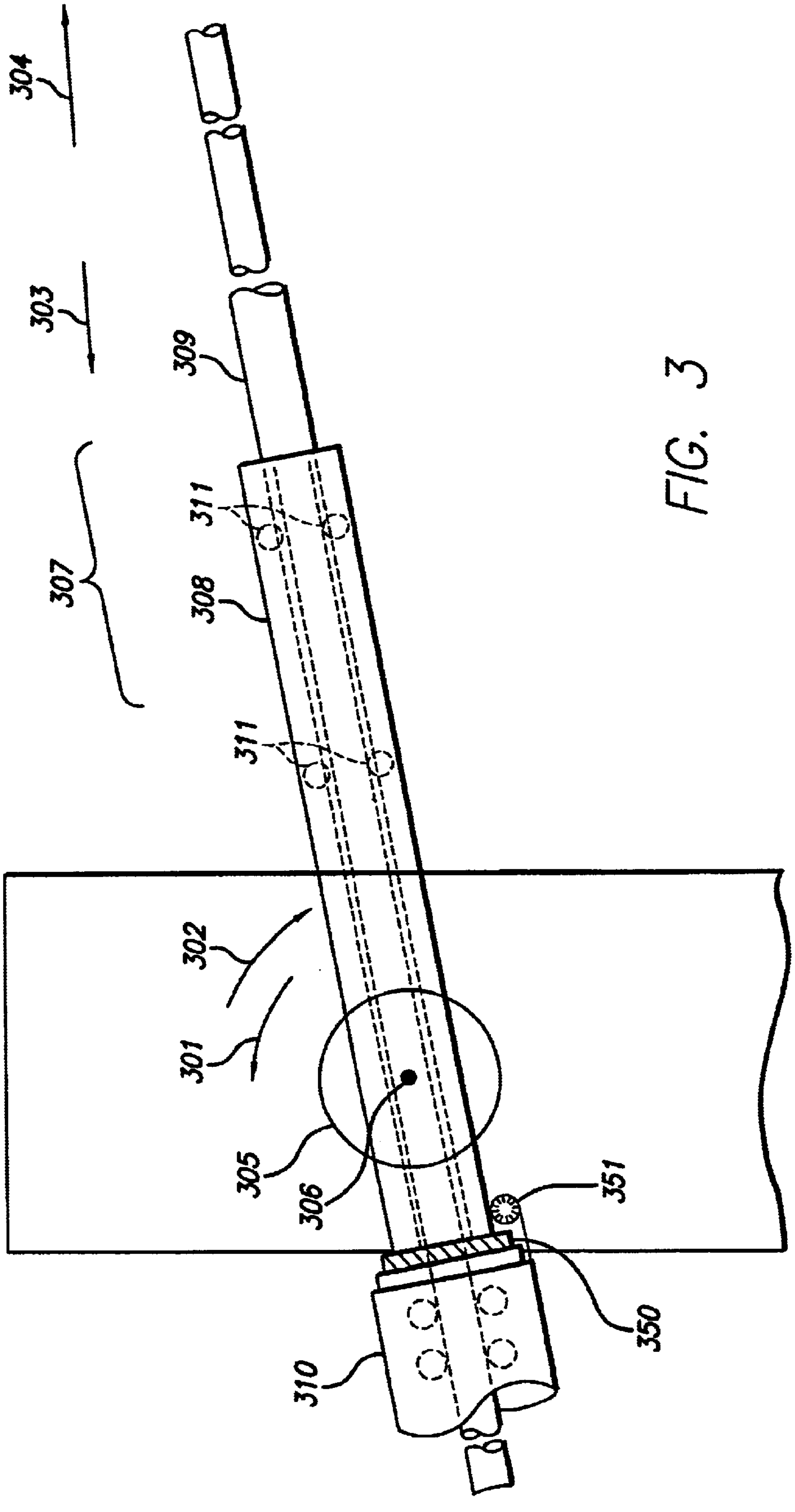
FIG. 3 shows a detail of one of the robotic arms with its rotary and telescopic motions.

As shown in FIG. 3, the first (or base) d.o.f (degree of freedom, or, joint) of the robot arms is rotational 301, 302, and the second (or subsequent) d.o.f, or, joint is linear of telescoping nature 303, 304. The rotational drive elements 105, 106, 107, 108 are represented by 305 in FIG. 3. The angular rotational motion indicated by the arrows 301 and 302 take place around a pivot point 306. This motion is driven by a motor 307 which is located perpendicular to the plane of rotation 301, 302 of the telescoping arm 307, in this aspect of this embodiment. The telescoping arm comprises an outer sleeve part 308 and an inner sleeve part 309. In addition a motor 310 for moving the inner sleeve relative 309 to the outer sleeve 308, which in this aspect of this embodiment is fixed to the rotating element 305. It should be noted that there are other ways, old in the art, of achieving the two dimensional motion in a plane which the rotating 301, 302, telescoping 303, 304 arm, as just described, which may form a different embodiment as herein presented, but which is equally good at providing the required (motor driven) degrees of freedom.

The mechanical part of the system uses four such robot arms. (101, 102), (103, 104), two for assisting each. leg of a patient in bipedal locomotion. The two arms are located above each other in a vertical plane coinciding with the sagittal plane of bipedal locomotion.

The rotational axis of the first joint 305 is perpendicular to the vertical (sagittal) plane while the linear (telescoping) axis 307 of the second joint is parallel to the vertical (sagittal) plane. Thus, the free end of each arm 111, 112, 113, 114 can move up-down and in-out. These motion capabilities are needed for each arm to jointly reproduce the profile of bipedal locomotion in the sagittal plane from a fixed treadmill 110 base 109 which is external to the act of bipedal locomotion on a treadmill 110.

FIG. 4 shows the patients leg A1. A leg support brace 400 is attached to the part of the leg A1 which is above 403 the knee and to the part of the leg below 404 the knee. As shown there is a freely pivoting pivot joint 401 corresponding the motion of the knee. The leg brace may correspond to a modified commercially available brace such as the C180 PCL (posterior tibial translation) support offered by Innovation Sports, with a modification. The modification to the leg support brace is shown as 407. The ankle has a padded custom-made attachment. In addition, a special shoe 405 containing pressure sensors 406 is used on the foot to provide feedback information to the main computer 115.

The arms 101 and 102 attach respectively for patient's leg A1 at the sensor 451 at the knee via the modification 407 and to the ankle area sensor 452. The exoskeleton supports and moves each leg so as to provide pressure on extensor surface during stance and flexor surface during swing. The extensor pressure is applied inferior to the patella in the vicinity of the patella tendon which helps locks the knee so as to aid "stance" position of the leg. The flexor pressure is applied in the vicinity of the hamstring muscles and associated tendons, on the back of the upper leg just above the rear crease of the knee, aiding in the "swing" part of the step motion.

An important additional feature is the continuous recording of the electrical activity of the muscles in the form of electromyograms (EMGs). These are real-time recordings of the electrical activity of the muscles measured with surface electrodes, or, optionally, with fine wire electrodes, or with a mix of electrode types.

The two arms 101, 102 assisting one leg are connected to the leg so that the lower arm is attached to the lower limb slightly above the ankle while the upper arm is attached to the leg near and slightly below the knee. This robot arm arrangement closely imitates a therapist's two-handed interaction with a patient's one leg A1 during locomotor training on a treadmill. Implied in this robot arm arrangement is the fact that the lower arm 102 is mostly responsible for the control of the lower limb while the upper arm 101 is mostly responsible for the upper limb control, though in a coordinated manner, complying with the profile of bipedal locomotion in the sagittal plane as seen from the front.

At the front end of each robot arm 101, 102, 103, 104 near the exoskeleton connection to the leg a combined force/torque and acceleration sensor 451, 452 (other two sensors of this type not shown) is mounted which measures the robot arm's interaction with the leg. Potentiometers 350 measuring the arm's position are installed at the drive motors at the base of the robot arms. Alternative methods, old in the art, also may be used, including but not limited to, a digitally-read rotating optical disk 351.

The mechanical elements necessary to properly connect to a variety of legs are adjustable to the geometry of individual patients, including the compliant elements of the system. The described four-arm architecture permits all active drive elements of each arm (motors, electronics, computer) to be housed on the front end of the treadmill 110 in a safe arrangement and safe operation modality. Aspects of the safe operation modality include limiting switches on the range of motion of the telescoping movements and in the rotating movements of the arms, emergency cut-off switches for both a monitoring therapist and for the patient. In addition, the leg brace 400 is constructed so that the pivoting joint 401 cannot be bent back so as to hyperextend the knee and destroy it. The overall construction of the leg brace 400 is such that it can resist a chosen safety factor, such as four times (4×), the maximum amount of force which the robotic arms with all their motors, can exert to buckle the knee, i.e., the constructed knee joint (for the C180, it is a four bar linkage), which protects the knee from hyperextension.

Figure 5:
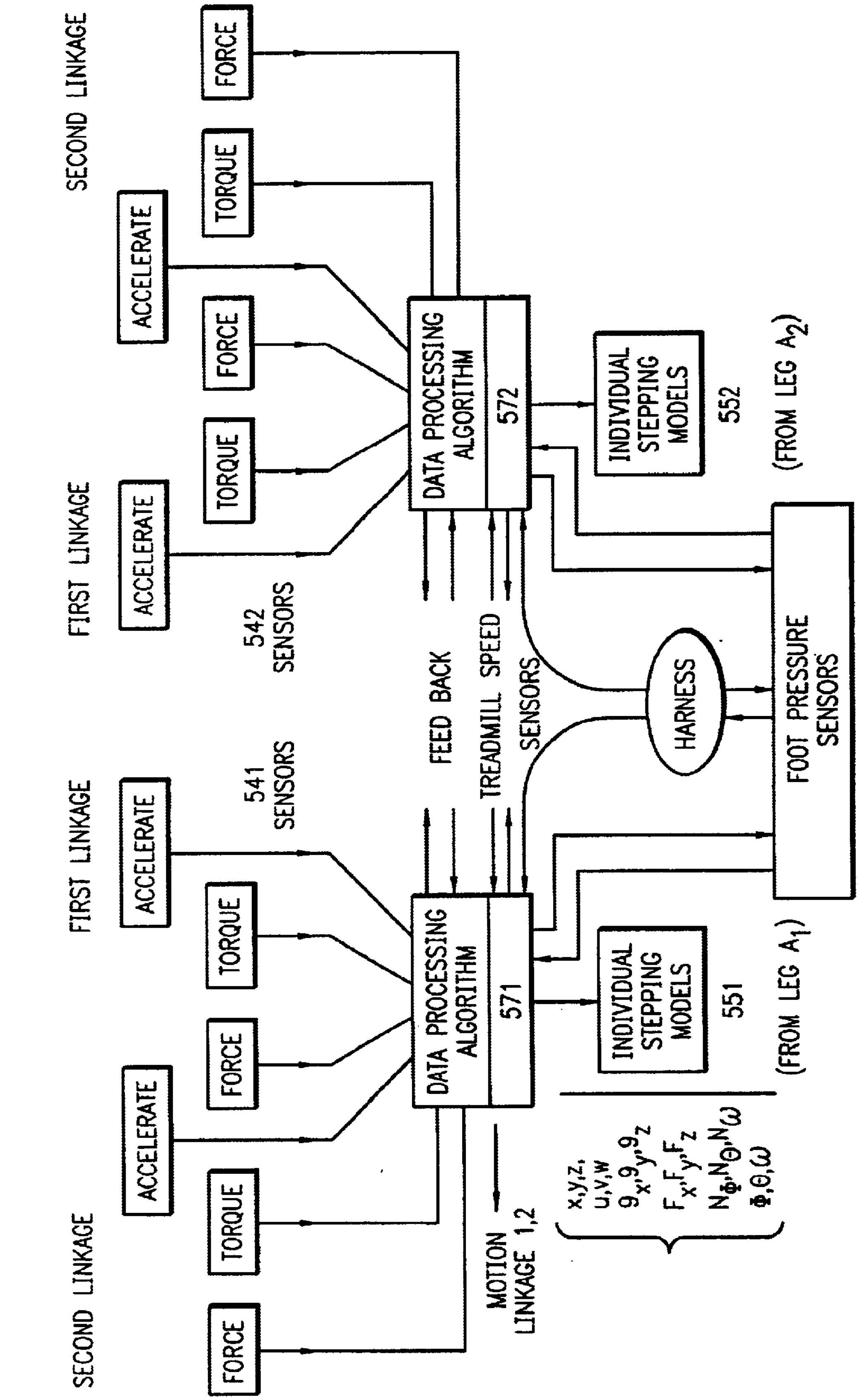
FIG. 5 shows a diagrammatic representation of the interactions of the sensors, treadmill speed, individual stepping models, and the computational and other algorithms which form the operating control with feedback part of the system.

The range of kinematic and dynamic parameters associated with the programmable stepping device (PSD) operation are determined from actual measurements of the therapists' interaction with the legs of various patients during training and from the ideal models, FIG. 5, 551, 552 of corresponding healthy persons' bipedal locomotion. The system can monitor and control each leg independently.

The control system (FIG. 5, 500) of the PSD is not wired to patients body but rather gets feedback from sensors in the vicinity of the ankles (FIG. 4B) 452, the knees 451 and from the (dynamic) pressure sensors 406 in the "shoes" of the apparatus.

The control system (FIG. 5, 500) is computer based and referenced to (i) individual stepping models 551, 552, (ii) treadmill speed 561, and (iii) force/torque/accelerometer sensor data 541 542 measured at the output end of each robot arm. The control software architecture 571, 572 is "intelligent" in the sense that it can distinguish between the force/torque generated by the patient's muscles, by the treadmill 110, and by the robot arms' drive motors 310 (others not shown) in order to maintain programed normal stepping on the treadmill.

Figure 6:
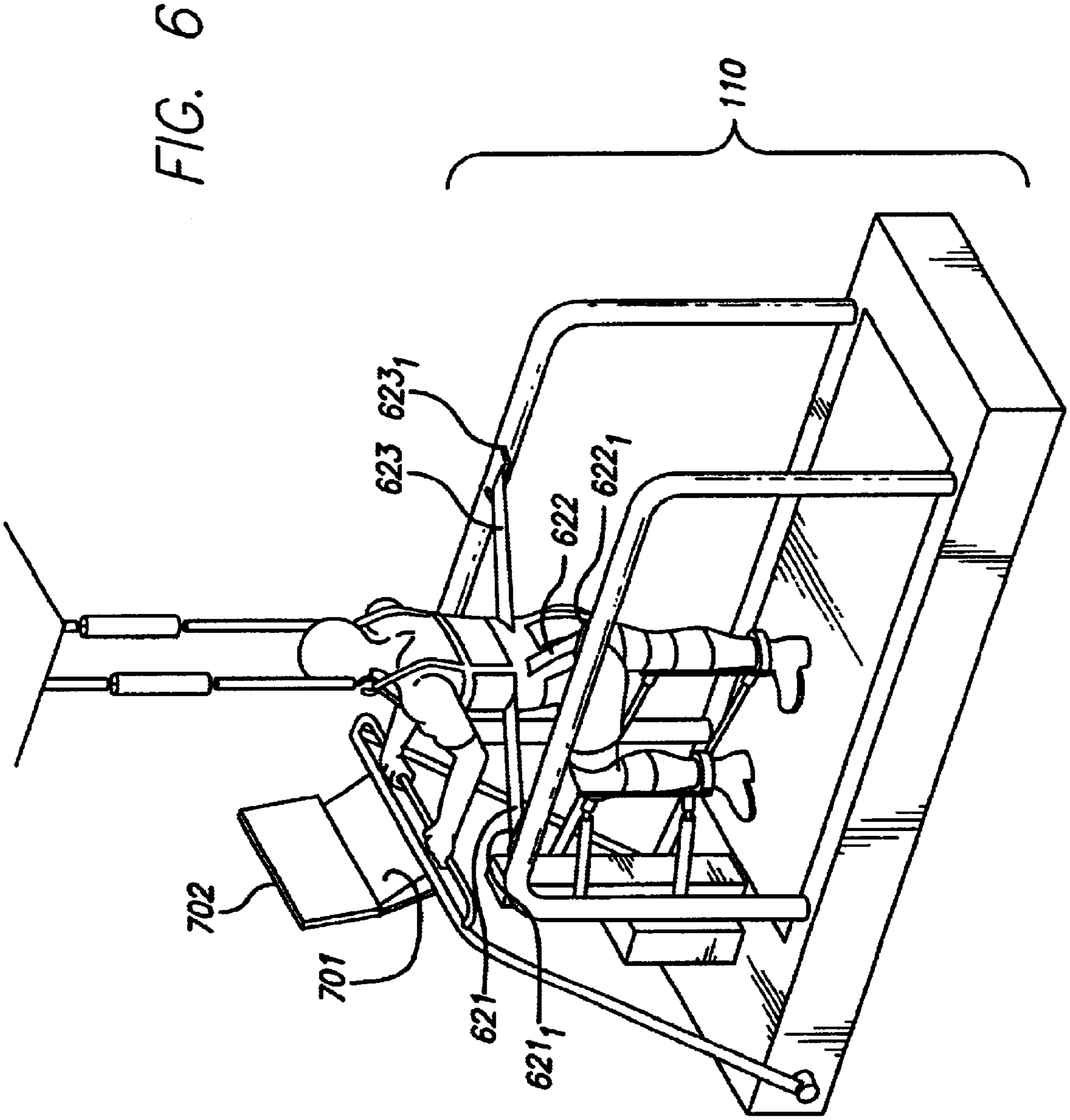
FIG. 6 shows the system of FIG. 1 from a rear three-quarter view showing details of the keyboard, display, and hip harness system, both passive and active.
Figure 7:
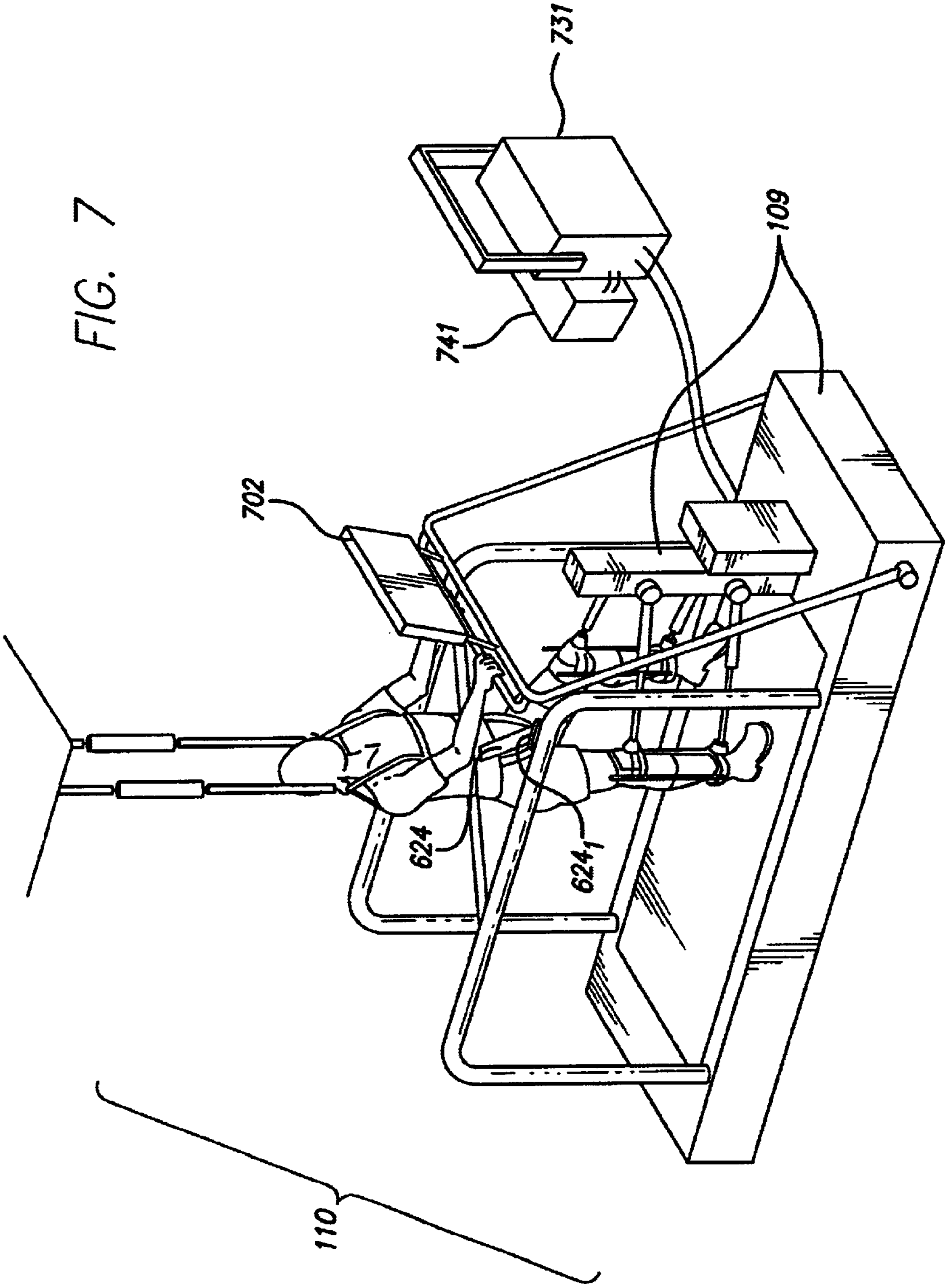
FIG. 7 shows the front three-quarter view corresponding to FIGS. 1 and 6, showing other detail of the hip control, system and the off-treadmill recording, display, and off-treadmill control part of the system.
Figure 8:
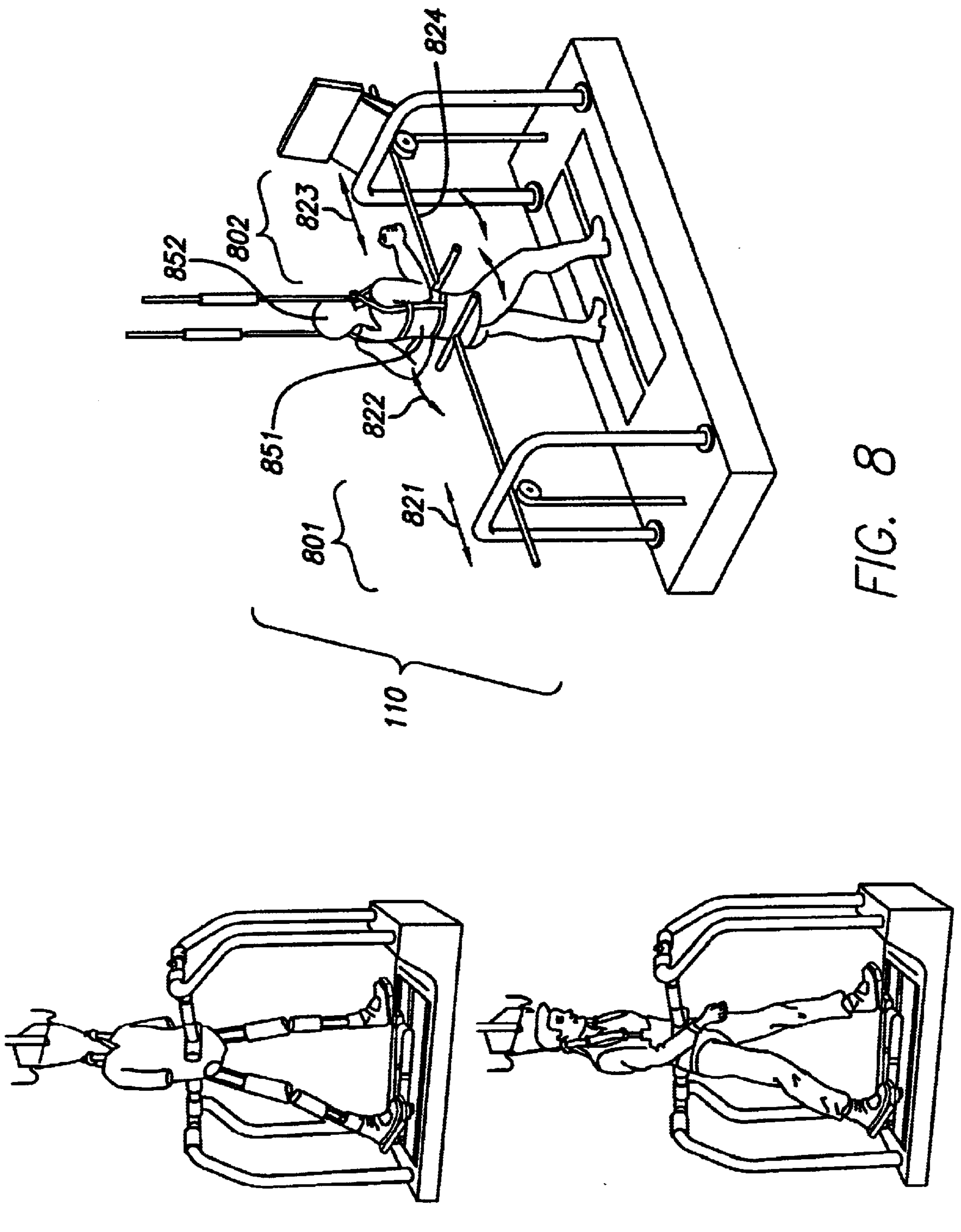
FIG. 8 shows a dual t-bar method for on-treadmill control of hip and body position.

The patient's contact force with the revolving treadmill belt is pre-adjustable through the BEST harness (FIG. 6, FIG. 7, 600) dependent upon body weight and size. The proper adjustment can be automatically maintained during motion by utilizing a proper force/pressure system on the harness 600. The harness system may be passive with respect to the hip placement of the patient, in so far as it provides for constraint via somewhat elastic belts, or cords, (FIG. 6) 621, 622, 623; (FIG. 7) 624. A more active adjustment system is also used, in a different aspect of an embodiment of this invention. FIG. 8 shows the use of dual T-bars 801 and 802 where the T-bars are adjustable, as shown by the curved and straight arrows, by controlled motors 821, 822, 823, 824. Other active methods of control of the hips, utilize stepping, or other, motors on the belts (FIG. 6) 621, 622, 623, as 6211, 6221, 6231) and (FIG. 7) 624 as 6241. The use of special sensor 406 shoes 405 also provides feedback for the adjustment of body weight in contact with the treadmill 110. The overall control system operates in E wireless configuration relative to the patient's body. The algorithms for the system include, in some aspects of an embodiment of the invention, neural network algorithms, in software and/or in hardware implementation, to "learn" aspects of the patient's gait, either when strictly mediated by the robotic system, or, when therapists move the patient through the "proper motions" while the robotic system is acting passively, except for measurements being made by sensors 406 and 451 and 452 and the electromyogram (EMG)s and the corresponding sensors on the other leg (not shown).

A keyboard (FIG. 6, 701) and monitor (FIGS. 6, 7) 702 attached to the treadmill 110 enables the user to input selected kinematic and dynamic stepping parameters to the computer-based control and performance monitor system. The term user, here, covers the patient and/or a therapist and/or a physician and/or an assistant. The user interface to the system is implemented by a keybord/monitor setup 701, 702 attached to the front of the treadmill 110, easily reachable by the patient, as long as the patient has enough use of upper limbs. It enables the user (therapist or patient) to input selected kinematic and dynamic stepping parameters and treadmill speed to the control and monitor system. A condensed stepping performance can also be viewed on this monitor interface in real time, based on preselected performance parameters.

An externally located digital monitor system 731 displays the patient's stepping performance in selected details in real time.

A data recording system 741 enables the storage of all training related and time based and time coordinated data, including electromyogram (EMG) signals, for off-line diagnostic analysis. The architecture of the data recording part of the system enables the storage of all training related and time based and time coordinated data, including electromyogram (EMG), torque and position signals, for off-line diagnostic analysis of patient motion, dependencies and strengths, in order to provide a comparison to expected patterns of nondisabled subjects. The system will be capable of adjusting or correcting for measured abnormalities in the patient's motion.

Figure 4A:
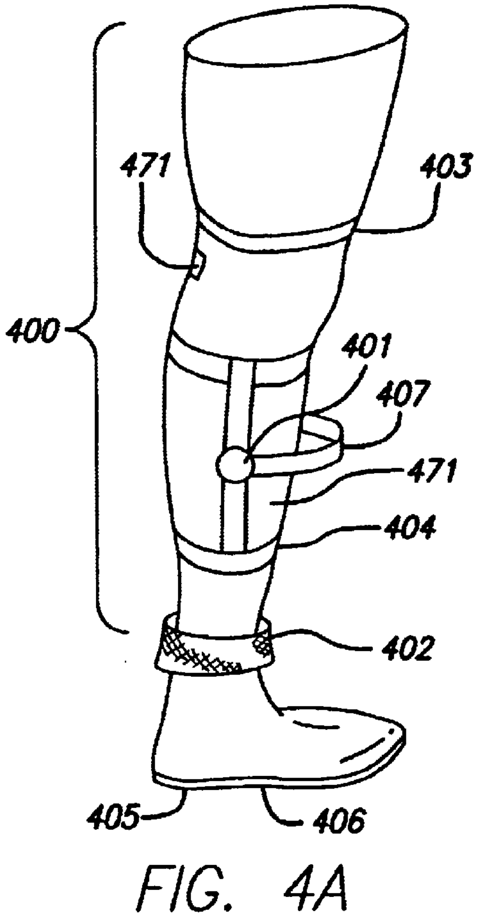
FIG. 4A shows, the detail of the ankle and upper leg attachments, as well as a special shoe with pressure sensors in it, and also shown are stimulation means for flexor and extensor muscle groups and tendons.
Figure 4B:
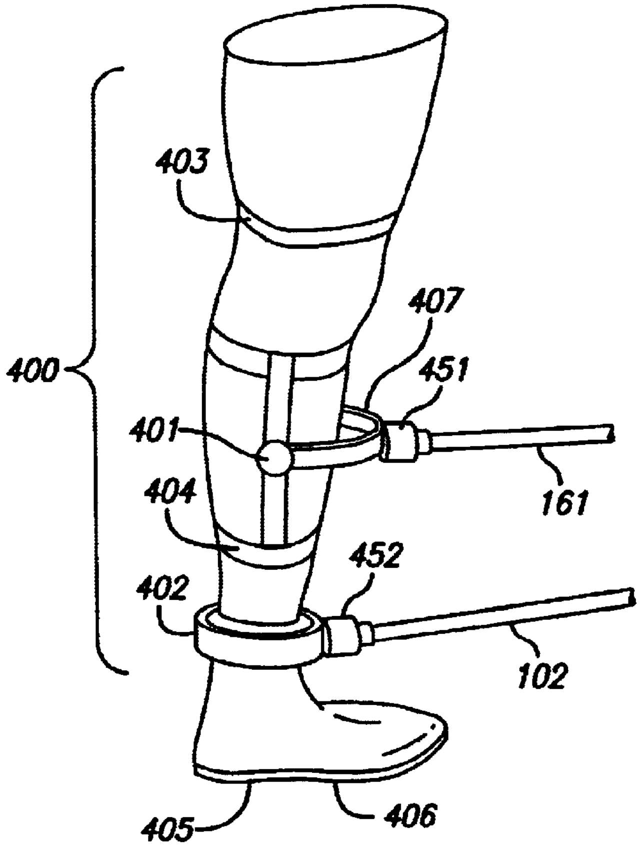
FIG. 4B shows a detail of corresponding to FIG. 4A, except that the robotic arms and the position of the sensor units are shown, attached between the arms and the ankle and knee attachments to the leg.

An important part of this embodiment of the invention is the provision for the extra-stimulation of designated and associated tendon group areas. For example, when the leg is being raised, flexor and associated tendons in the lower hamstring area on the back of the leg are optionally subject to vibration or another type of extra-stimulation.(See FIG. 4A, 471, 472) This is thought to strengthen the desired nerve pathways to allow the patient to develop toward overground locomotion. Therapeutic stimulators 471, 472, which may be vibrators, is shown in FIG. 4A.

The overall system is designed to minimize the external mechanical load acting on the patient while maximizing the work performed by the patient to generate effective stepping and standing during treadmill training.

Operation safety is assured by proper stop conditions implemented in the control software and in the electrical and mechanical control hardware. The patient's embarkment to and disembarkment from the Programmable Stepping Device (PSD) is a manual operation in all cases.

While the invention herein disclosed has been described by means of specific embodiments and applications thereof, numerous modifications and variations could be made thereto by those skilled in the art without departing from the scope of the invention set forth in the claims.

What is claimed is:

1. A system for assisting and easing the rehabilitation of spinal cord, stroke and traumatic brain injured people (as well as others with injury affecting locomotion) to regain walking capabilities comprising (a) an individually adjustable automated body weight suspension training system;

(b) multiple sensors wherein said sensors provide feedback to adjust the automated body weight suspension training system.

2. The system of claim 1 further comprising:

(a) two pairs of motor-driven mechanical linkage units;

(b) each of said units with two mechanical degrees-of-freedom;

(c) said units connected with their drive elements to a fixed base of a treadmill;

(d) said linkages' free ends wherein said free ends are attachable to the patient's legs at two locations at each leg; wherein one linkage pair serves one leg in the sagittal plane of bipedal locomotion; and wherein the other linkage pair serves the other leg in the sagittal plane of bipedal locomotion.

3. The system of claim 1 further comprising:

(a) an exoskeleton linkage system with its passive compliant elements wherein said exoskeleton linkage system with its passive compliant elements are adjustable to an individual patient's geometry and dynamics.

4. The system of claim 3 further comprising: said linkage system arrangement wherein said linkage system arrangement is capable of reproducing the profile of bipedal locomotion and standing in the sagittal plane, from a fixed base.

5. The system of claim 1 further comprising:

(a) a control system for a programmable stepping device;

(b) said computer based control system of a linkage system of the programmable stepping device;

(c) said control system referenced to individual stepping models, treadmill speed, and force, torque, electromyogram (EMG) and acceleration data;

(d) said data sensed at the linkages' exoskeleton contact area with each of the patient's legs.

6. The system of claim 1 further comprising:

(a) control algorithms of the exoskeleton linkages' computer control system (b) said control algorithms being "intelligent" control for biped locomotion wherein said algorithms distinguish between the amount and direction of the force/torque generated by the patient, by the feet's contact with the treadmill, and by the action of the programmable stepping device;

(c) said control system monitoring and controlling each leg independently.

7. The system of claim 1 further comprising:

said control system operating by way of feedback through sensors for force, torque, acceleration, and pressure located at various points on or in the exoskeleton system; wherein no wires are required to go to the human body.

8. The system of claim 1 further comprising:

a keyboard attached to the treadmill wherein the user, one or more, selected from the group consisting of patient, therapist, physician and assistant can input selected kinematic and dynamic stepping parameters to said computer-based control system.

9. The system of claim 1 further comprising:

an externally located digital monitor system wherein the patient's stepping performance is selectively displayed in real time.

10. The system of claim 1 further comprising:

a data recording system wherein the storage of all training related and time based and time coordinated data, including electromyogram (EMG) signals, for off-line diagnostic analysis is enabled.

11. The system of claim 1 further comprising:

(a) a minimized external mechanical load acting on the patient;

(b) a maximized work performed by the patient in generating effective stepping and standing during treadmill training.

12. The system of claim 1 further comprising:

(a) a stimulator for applying stimulation to selected flexor muscles and associated tendons;

(b) a stimulator for applying stimulation to selected extensor muscles and associated tendons.

13. The system of claim 12 wherein said stimulators for applying stimulation to selected flexor and extensor muscles and associated tendons are vibrating stimulators.

14. The system of claim 1 further comprising:

an active system for positioning the hips.

15. The system of claim 14 further comprising:

said active system wherein controlled dual T-bars position the hips.

16. The system of claim 14 further comprising:

said active system wherein motorized semi-elastic belts position the hips.

17. An apparatus for rehabilitation of spinal cord, stroke and traumatic brain injured people (as well as others with injury affecting locomotion) to regain walking capabilities comprising:

(a) an individually adjustable automated body weight suspension training apparatus;

(b) multiple sensors wherein said sensors provide feedback to adjust the automated body weight suspension training apparatus;

(c) two pairs of motor-driven mechanical linkage units;

(d) each of said units with two mechanical degrees-of-freedom;

(e) said units connected with their drive elements to a fixed base of a treadmill;

(f) said linkages' free ends wherein said free ends are attachable to the patient's legs at two locations at each leg; wherein one linkage pair serves one leg in the sagittal plane of bipedal locomotion; and wherein the other linkage pair serves the other leg in the sagittal plane of bipedal locomotion.

18. The apparatus of claim 17 further comprising:

(a) an exoskeleton linkage system with its passive compliant elements wherein said exoskeleton linkage system with its passive compliant elements are adjustable to an individual patient's geometry and dynamics;

(b) said linkage system arrangement wherein said linkage system arrangement is capable of reproducing the profile of bipedal locomotion and standing in the sagittal plane, from a fixed base.

19. The apparatus of claim 17 further comprising:

(a) a control system for a programmable stepping device;

(b) said computer based control system of a linkage system of the programmable stepping device;

(c) said control system referenced to individual stepping models, treadmill speed, and force, torque, electromyogram (EMG) and acceleration data;

(d) said data sensed at the linkages' exoskeleton contact area with each of the patient's legs.

20. The apparatus of claim 17 further comprising:

(a) control algorithms of the exoskeleton linkages' computer control system (b) said control algorithms being "intelligent" control for biped locomotion wherein said algorithms distinguish between the amount and direction of the force/torque generated by the patient, by the feet's contact with the treadmill, and by the action of the programmable stepping device;

(c) said control system monitoring and controlling each leg independently;

(d) said control system operating by way of feedback through sensors for force, torque, electromyogram (EMG), acceleration, and pressure located at various points on or in the exoskeleton system; wherein no wires are required to go to the human body.

21. The apparatus of claim 17 further comprising:

(a) a keyboard attached to the treadmill wherein the user, one or more, selected from the group consisting of patient, therapist, physician and assistant, can input selected kinematic and dynamic stepping parameters to said computer-based control system;

(b) an externally located digital monitor system wherein the patient's stepping performance is selectively displayed in real time;

(c) a data recording system wherein the storage of all training related and time based and time coordinated data, including electromyogram (EMG) signals, for off-line diagnostic analysis is enabled.

22. The apparatus of claim 17 further comprising:

(a) a minimized external mechanical load acting on the patient;

(b) a maximized work performed by the patient in generating effective stepping and standing during treadmill training.

23. The system of claim 17 further comprising:

(a) a stimulator for applying stimulation to selected flexor and associated tendons;

(b) a stimulator for applying stimulation to selected extensor muscles and associated tendons.

24. The system of claim 23 wherein said stimulators for applying stimulation to selected flexor and extensor muscles are vibrating stimulators.

25. The apparatus of claim 17 further comprising:

an active system for positioning the hips.

26. The apparatus of claim 25 further comprising:

said active system wherein controlled dual T-bars position the hips.

27. The apparatus of claim 25 further comprising:

said active system wherein motorized semi-elastic belts position the hips.

* * * * *